US012702769B2

(12) United States Patent
Fabien

(10) Patent No.: US 12,702,769 B2
(45) Date of Patent: Aug. 11, 2026

(54) DEVICE FOR DISPENSING A FLUID PRODUCT

(71) Applicant: APTAR FRANCE SAS, Le Neubourg (FR)

(72) Inventor: David Fabien, Saint Renan (FR)

(73) Assignee: APTAR FRANCE SAS, Le Neubourg (FR)

( * ) Notice: Subject to any disclaimer, the term of this patent is extended or adjusted under 35 U.S.C. 154(b) by 845 days.

(21) Appl. No.: 18/011,393

(22) PCT Filed: Jun. 18, 2021

(86) PCT No.: PCT/FR2021/051108
§ 371 (c)(1),
(2) Date: Dec. 19, 2022

(87) PCT Pub. No.: WO2021/260305
PCT Pub. Date: Dec. 30, 2021

(65) Prior Publication Data

US 2023/0302239 A1 Sep. 28, 2023

(30) Foreign Application Priority Data

Jun. 22, 2020 (FR) ...................................... 2006490

(51) Int. Cl.
*A61M 15/08* (2006.01)
*A61M 15/00* (2006.01)
(Continued)

(52) U.S. Cl.
CPC .......... *A61M 15/08* (2013.01); *A61M 15/009* (2013.01); *A61M 2205/103* (2013.01);
(Continued)

(58) Field of Classification Search
CPC .............. A61M 15/08; A61M 15/0081; A61M 15/0083; A61M 15/009; A61M 15/0095;
(Continued)

(56) References Cited

U.S. PATENT DOCUMENTS 5,228,586 A 7/1993 Fuchs
2010/0084433 A1* 4/2010 Cater .................. B05B 11/1059 222/153.13

(Continued)

FOREIGN PATENT DOCUMENTS

EP 0114617 A2 8/1984

OTHER PUBLICATIONS

International Preliminary Report on Patentability dated Dec. 13, 2022 in Application No. PCT/FR2021/051108.

(Continued)

*Primary Examiner* — Valerie L Woodward
*Assistant Examiner* — Maurin I Ashimiu
(74) *Attorney, Agent, or Firm* — Sughrue Mion, PLLC

(57) ABSTRACT

A device having dispenser with a reservoir containing fluid product and a dispensing mechanism, an internal body with a hollow cylinder receiving the dispenser, an actuator with a dispensing orifice, the axial displacement of the actuator from its rest position towards its actuating position actuating the dispensing mechanism to dispense a dose of fluid product, a motor, an electronic control module, a gear wheel connected to the motor and driven by the motor, and a locking ring rotatably mounted on the internal body between a locking position and a release position, a spring urging the locking ring towards its locking position, the locking ring displaced from its locking position towards its release position by the gear wheel, the locking ring cooperating with the actuator in the locking position to prevent its axial displace- (Continued)

Figure 1:
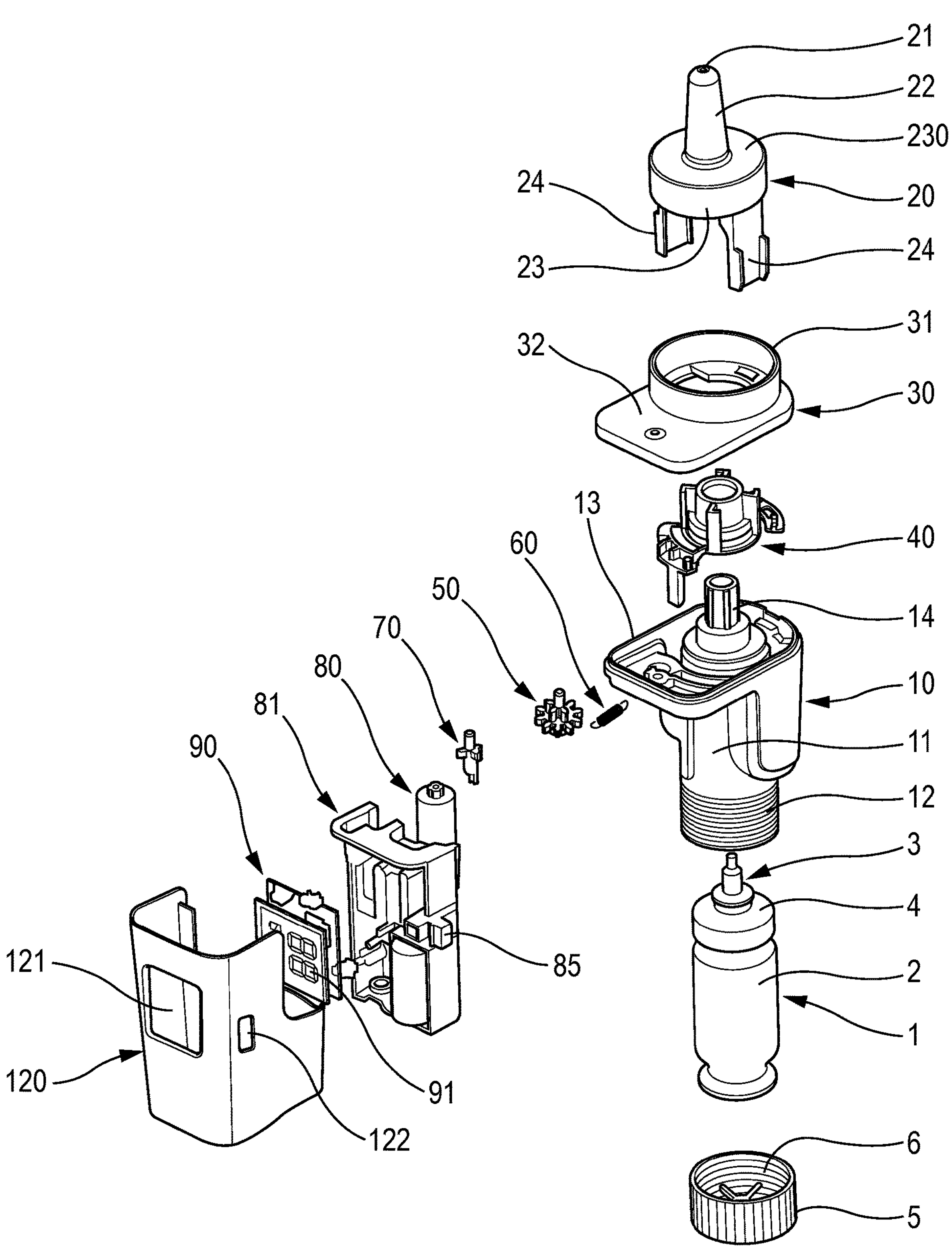

ment and cooperating with the actuator in the release position to enable displacement towards its actuating position.

15 Claims, 8 Drawing Sheets

(51) Int. Cl.
*B05B 11/00* (2023.01)
*B05B 12/02* (2006.01)
*B65D 83/22* (2025.01)
*B65D 83/384* (2025.01)

(52) U.S. Cl.
CPC ................ *A61M 2205/276* (2013.01); *A61M 2205/8275* (2013.01)

(58) Field of Classification Search
CPC .... A61M 11/006–008; A61M 2205/27; A61M 2205/276; B05B 11/1059; B05B 11/106
See application file for complete search history.

(56) References Cited

U.S. PATENT DOCUMENTS

2015/0320948 A1 11/2015 Eicher et al.
2022/0379046 A1* 12/2022 Decock ................ A61M 15/08
2022/0387721 A1* 12/2022 Decock ................ G16H 20/13

OTHER PUBLICATIONS

International Search Report for PCT/FR2021/051108 dated Sep. 30, 2021.

* cited by examiner

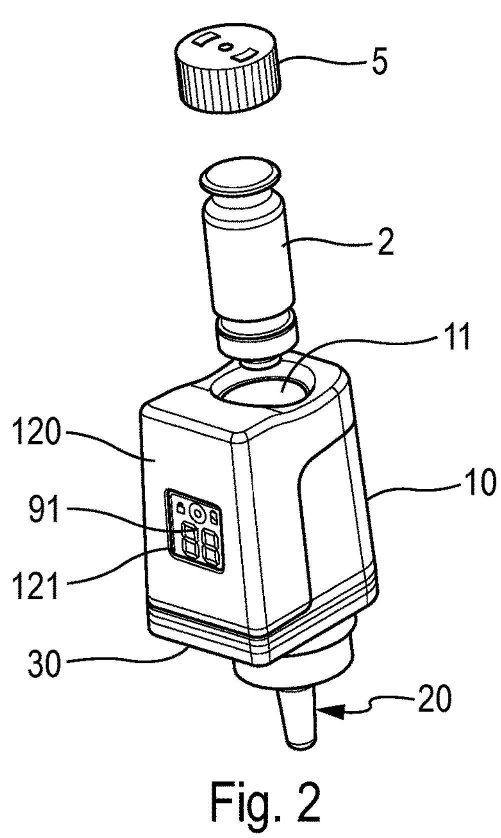
Fig. 2
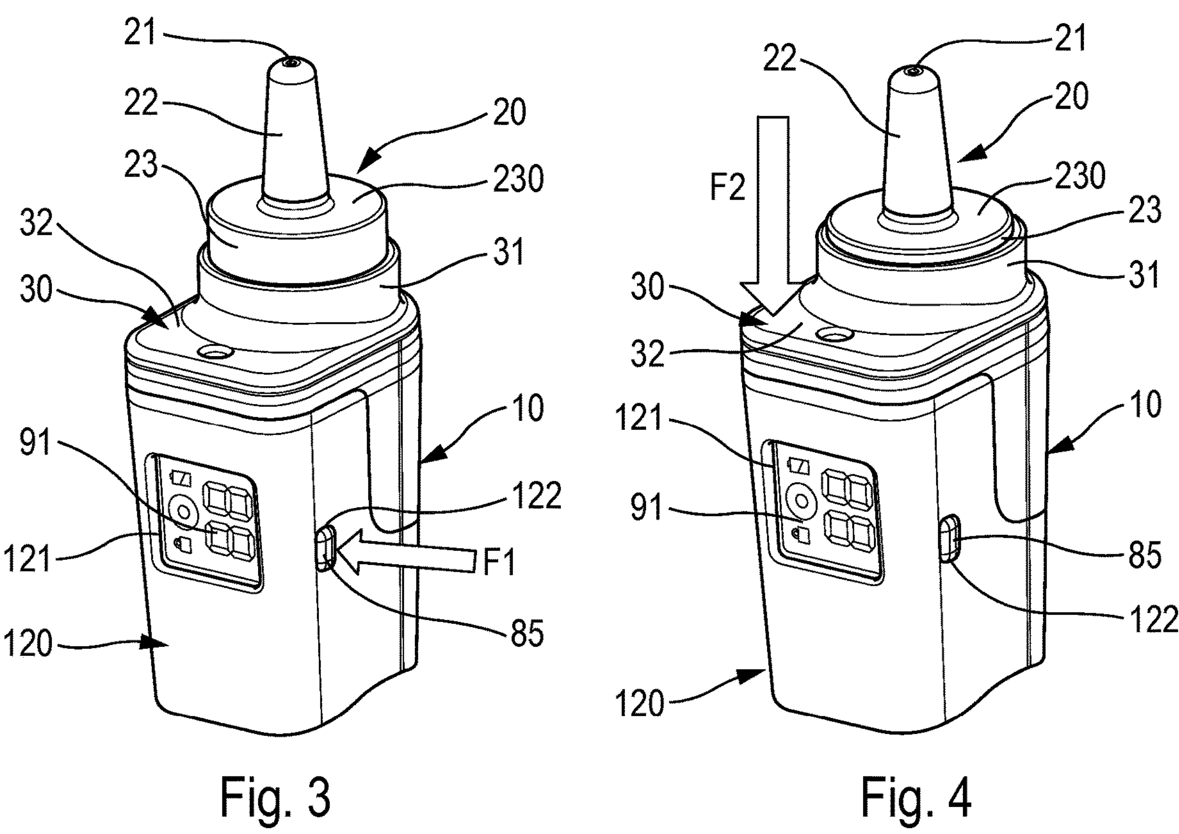
Fig. 3
Fig. 4

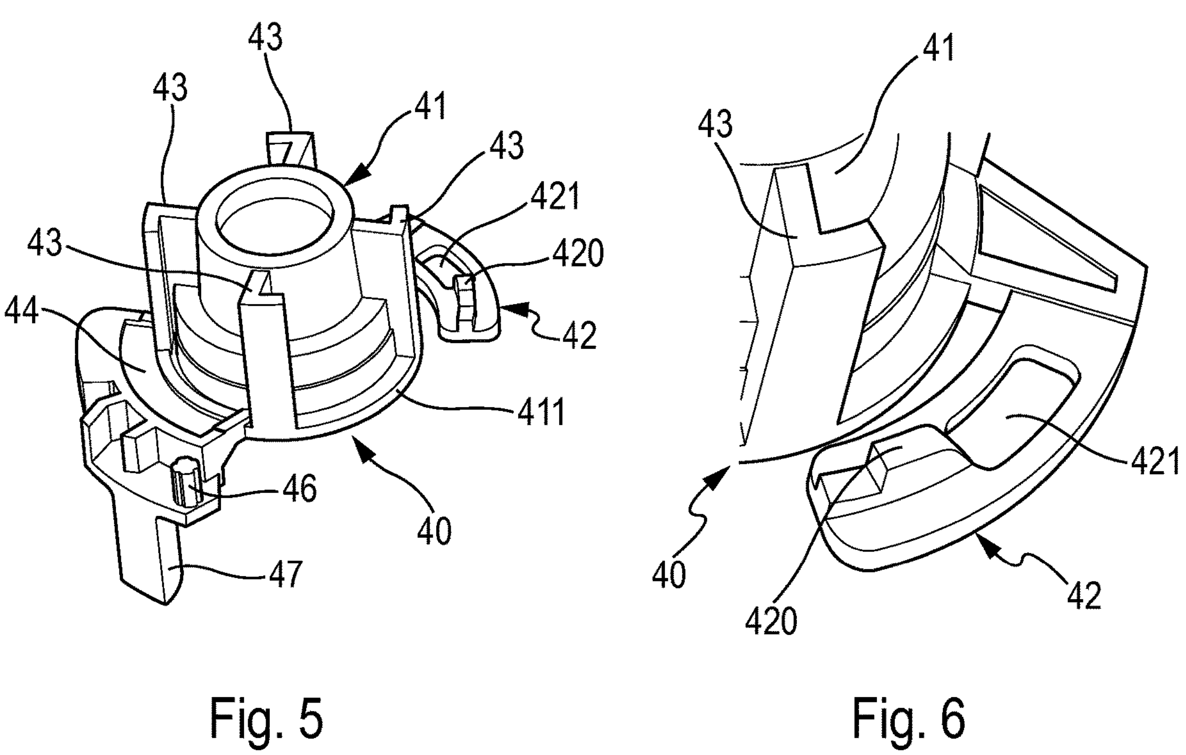
Fig. 5
Fig. 6
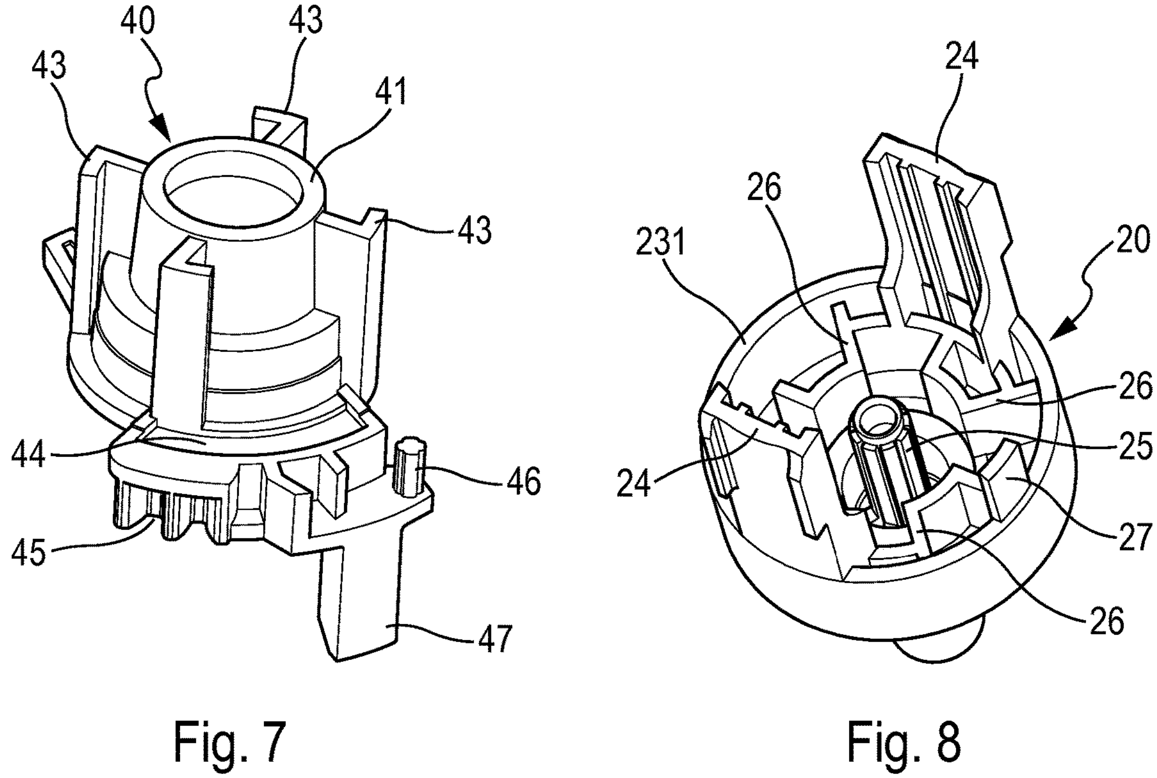
Fig. 7
Fig. 8

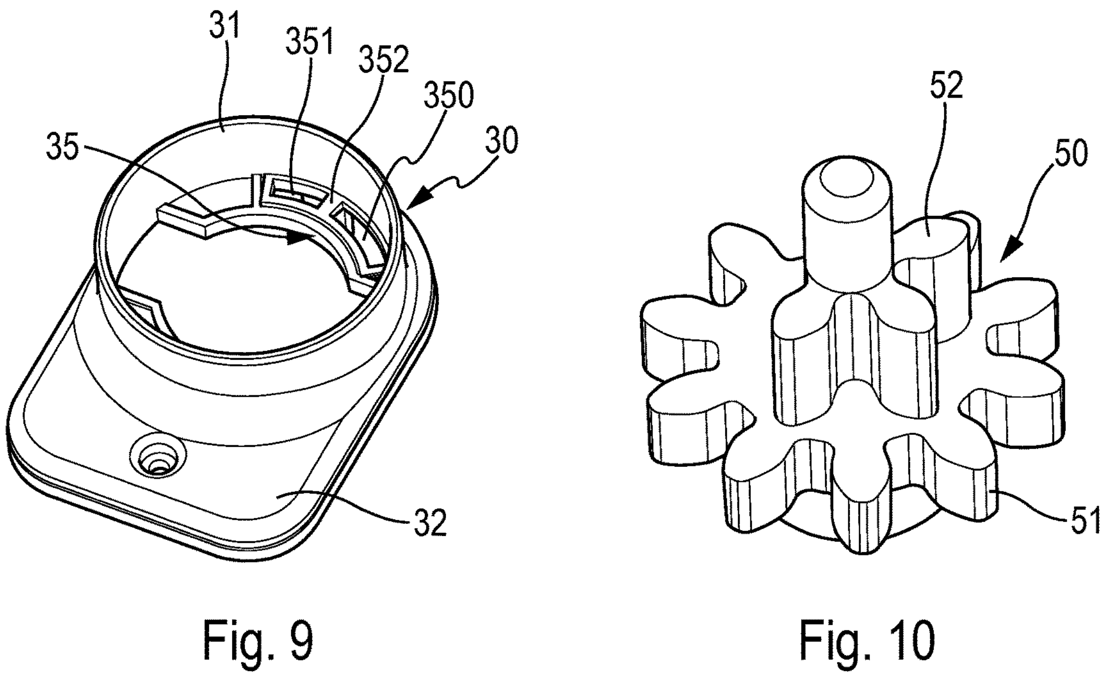
Fig. 9
Fig. 10
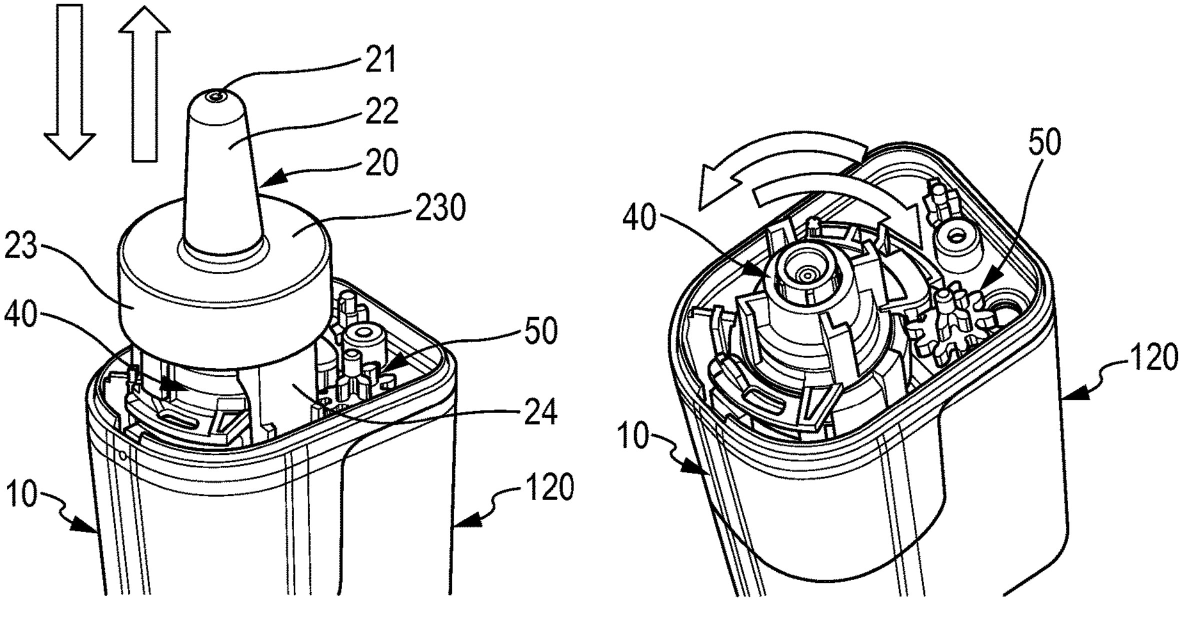
Fig. 11
Fig. 12

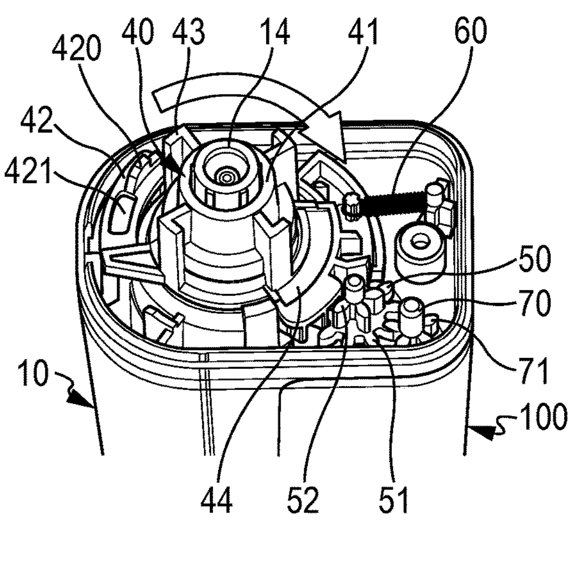
Fig. 13
Fig. 14
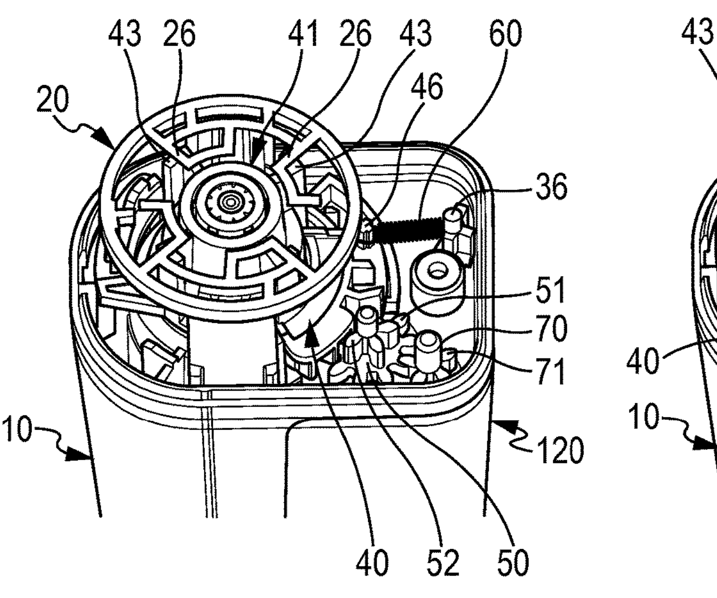
Fig. 15
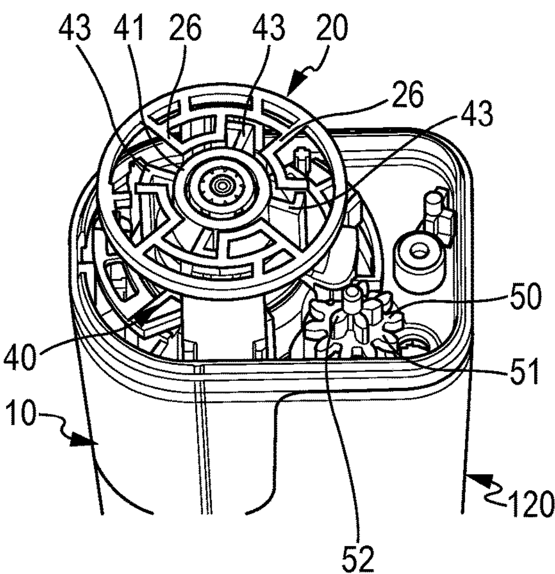
Fig. 16

DEVICE FOR DISPENSING A FLUID PRODUCT

CROSS REFERENCE TO RELATED APPLICATIONS

This application is a National Stage of International Application No. PCT/FR2021/051108 filed Jun. 18, 2021, claiming priority based on French Patent Application No. 2006490 filed Jun. 22, 2020.

The present invention relates to a device for dispensing a fluid product.

At present, the administration of potent drugs which are potentially lethal to human beings may be a necessity in certain situations. This is particularly the case for the treatment of particular diseases, or indeed for people in need of palliative treatment in end-of-life contexts. Handling such substances requires great caution and extremely safe administration devices in order to avoid the risk of overdoses which may occur in the event that several consecutive doses are administered close together.

Document U.S. Pat. No. 5,228,586 describes a dispenser as described in the preamble of claim 1. Documents EP 0 114 617 and US 2015/320948 describe other prior art devices.

The aim of the present invention is to provide a device for dispensing a fluid product which does not suffer from the aforementioned disadvantages.

In particular, the aim of the present invention is to provide a device for dispensing a fluid product which is safe and which safeguards the user, in particular in order to avoid the risk of overdose.

Another aim of the present invention is to provide a device for dispensing a fluid product which is immobilized for a predeterminable period of time between two successive actuations.

Another aim of the present invention is to provide a device for dispensing a fluid product which is robust and reliable in use.

A further aim of the present invention is to provide a device for dispensing a fluid product which is simple and inexpensive to manufacture and assemble.

The present invention therefore provides a device for dispensing a fluid product comprising:

- a fluid product dispenser comprising a reservoir containing fluid product and a dispensing means, such as a pump or a valve, mounted on said reservoir,
- an internal body comprising a hollow cylinder receiving said dispenser,
- an actuator provided with a dispensing orifice, axially displaceably mounted on said internal body between a rest position and an actuating position, the axial displacement of said actuator from its rest position towards its actuating position actuating said dispensing means in order to dispense a dose of fluid product through said dispensing orifice,
- a motor,
- an electronic control module,
- a gear wheel connected to said motor and driven in rotation by said motor, and
- a locking ring which is rotatably mounted on said internal body between a locking position and a release position, a spring urging said locking ring towards its locking position, said locking ring being displaced from its locking position towards its release position by said gear wheel, said locking ring cooperating with said actuator in the locking position in order to prevent its axial displacement and cooperating with said actuator in the release position in order to enable its axial displacement towards its actuating position.

Advantageously, the device comprises an external body fixed to said internal body and containing said motor and said electronic control module.

Advantageously, the device comprises a control button for initiating the actuation of said motor.

Advantageously, said actuator comprises at least one axial strut and said locking ring comprises at least one radial projection.

Advantageously, in the locking position of said locking ring, said at least one radial projection cooperates with said at least one axial strut in order to prevent said actuator from being displaced axially towards its actuating position, and in the release position of said locking ring, said at least one radial projection is angularly offset from said at least one axial strut, thereby enabling said actuator to be displaced axially towards its actuating position.

Advantageously, the device comprises four radial projections and four axial struts, each radial projection cooperating with a respective axial strut in order to immobilize the axial displacement of said actuator in the locking position of said locking ring.

Advantageously, said locking ring comprises an axially flexible tongue provided with an axially upwardly projecting tooth.

Advantageously, said internal body, or an element which is integral with said internal body, such as a cover, comprises an internal profile comprising a first window and a second window which is separated from said first window by a radial strut.

Advantageously, said actuator comprises an axially downwardly extending axial finger.

Advantageously, in the locking position of said locking ring, said tooth is disposed in said first window, the displacement of said locking ring towards its release position axially deforming said flexible tongue in order to enable said tooth to pass into the second window, behind said radial strut, said radial strut then cooperating with said tooth in order to prevent said locking ring from returning to the locking position under the effect of said spring.

Advantageously, during the axial displacement of said actuator from its rest position to its actuating position, said axial finger cooperates with said tooth by pushing it axially downwardly in order to disengage it from said radial strut, thereby enabling said locking ring to return to its locking position.

Advantageously, while said actuator is being displaced out of its rest position, said actuator immobilizes said locking ring in an intermediate position between its release position and its locking position.

Advantageously, at the end of actuation, when said actuator returns to its rest position, said locking ring returns automatically to its locking position under the effect of said spring.

Advantageously, said electronic control module comprises time delay means in order to prevent the displacement of said locking ring from its locking position towards its release position for a predeterminable time after each actuation of the dispenser.

Advantageously, said time delay means immobilizes a control button of the device and/or said motor.

Figures 17, 18, 19, 20, 21:
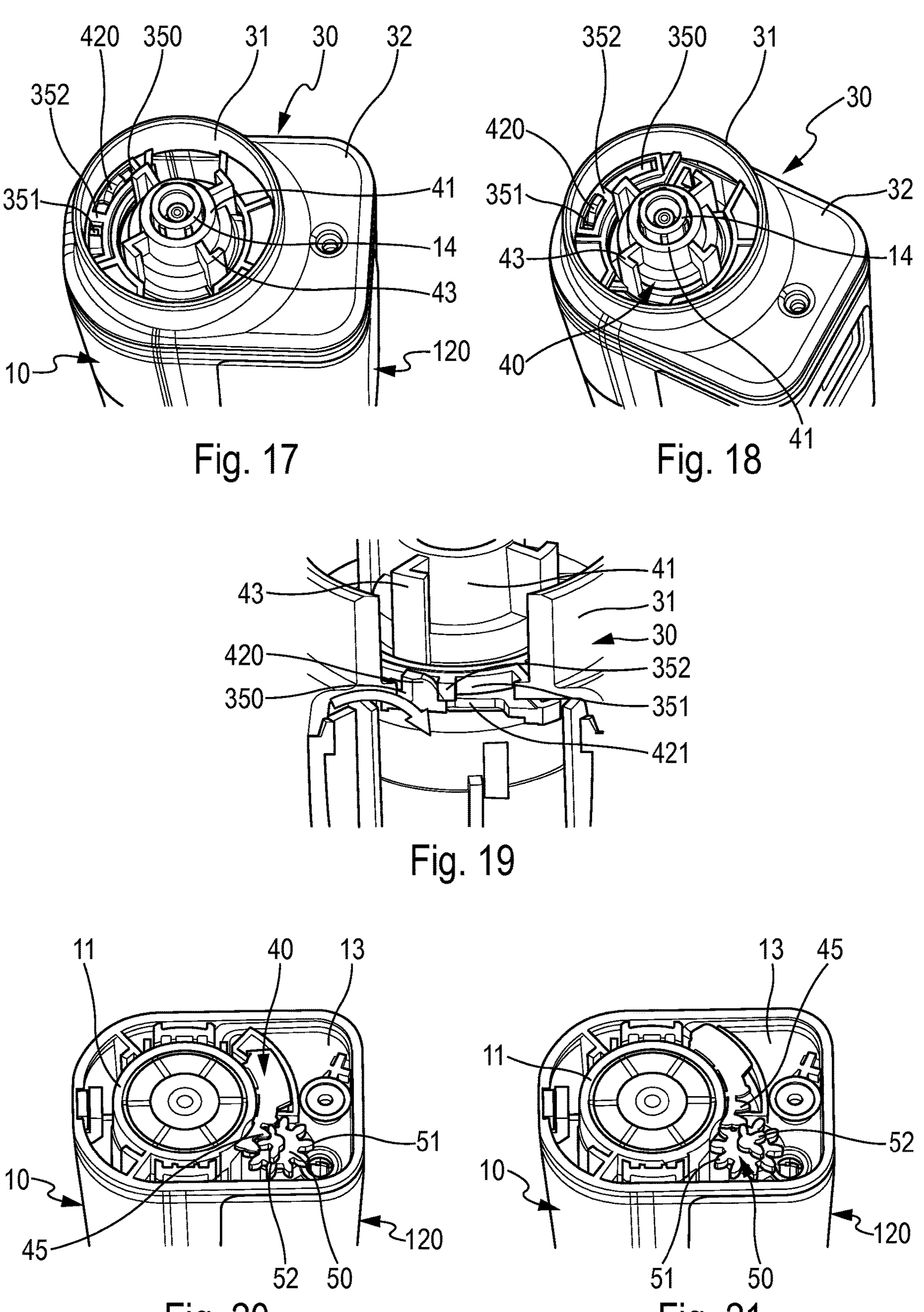
Figure 27:
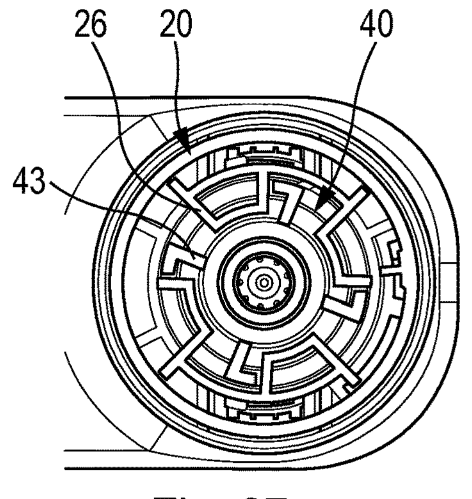
Figure 28:
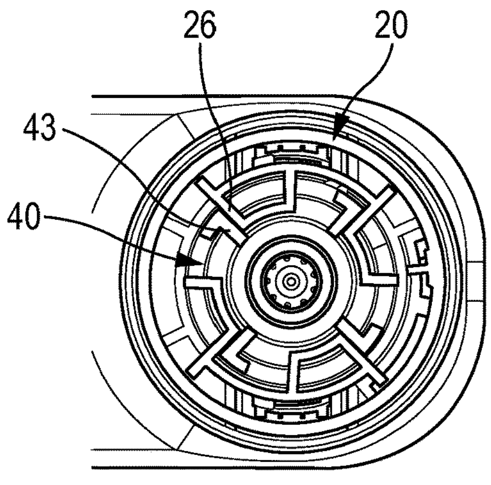
Figure 29:
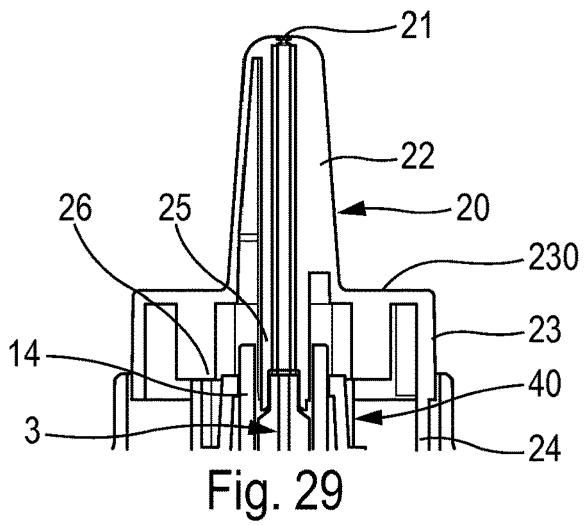
Figure 30:
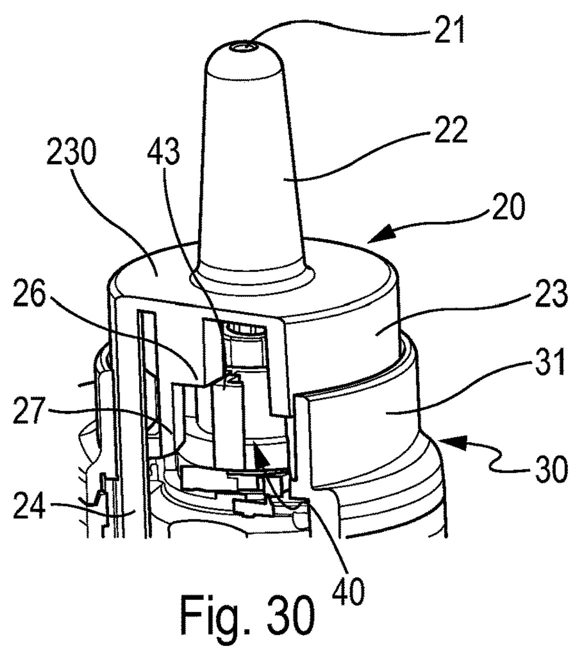
Figure 31:
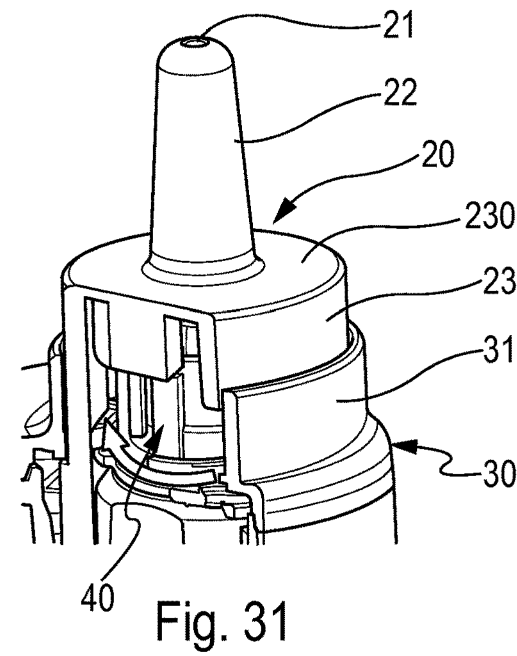

These features and advantages and others of the present invention will become more apparent from the following detailed description, given by way of non-limiting example and with reference to the accompanying drawings, and in which:

FIG. 1 is a diagrammatic exploded perspective view of a dispensing device in accordance with an advantageous embodiment, FIG. 2 is a diagrammatic exploded perspective view illustrating the assembly of the fluid product dispenser in the device, FIG. 3 is a diagrammatic perspective side view of the device of FIG. 1, illustrating the step for unlocking the device, FIG. 4 is a view similar to that of FIG. 3, illustrating the step of actuating the fluid product dispenser, FIG. 5 is a diagrammatic perspective view of the locking ring in accordance with an advantageous embodiment, FIG. 6 is a diagrammatic perspective view in detail of a portion of the locking ring of FIG. 5, FIG. 7 is a diagrammatic view similar to that of FIG. 5, from another viewing angle, FIG. 8 is a diagrammatic perspective view from below of the actuator, FIG. 9 is a diagrammatic perspective view of the cover in accordance with an advantageous embodiment, FIG. 10 is a diagrammatic perspective view of the gear wheel in accordance with an advantageous embodiment, FIG. 11 is a partial diagrammatic perspective view showing the axial displacement of the actuator during actuation, FIG. 12 is a diagrammatic view similar to that of FIG. 11, showing the displacement in rotation of the locking ring during unlocking, FIG. 13 is a diagrammatic cutaway perspective view showing the locking ring urged towards its locking position, FIG. 14 is a diagrammatic cross sectional view showing the cooperation between the locking ring and the gear wheel, FIGS. 15 and 16 are diagrammatic cutaway perspective views which show the actuator, the locking ring and the gear wheel, respectively in the locking position and in the release position, FIGS. 17 and 18 are diagrammatic cutaway perspective views which show the locking ring in the locking position and release positions respectively, FIG. 19 is a diagrammatic cutaway perspective view in detail showing the flexible tab of the locking ring in the locking position, FIGS. 20 and 21 are diagrammatic cutaway perspective views which show the cooperation between the locking ring and the gear wheel during an unlocking cycle, FIGS. 22 to 26 are diagrammatic cutaway perspective views in detail which show the flexible tab during an actuation cycle of the device, FIGS. 27 and 28 are diagrammatic horizontal cross-sectional views which show the locking ring respectively in the release position and in the intermediate position during actuation of the device, FIG. 29 is a diagrammatic vertical cross-sectional view of the actuator before it returns to the rest position, and FIGS. 30 and 31 are diagrammatic partially cutaway perspective views showing the locking ring returning to the locking position at the end of actuation, when the actuator returns to the rest position.

The terms “axial”, “radial”, “horizontal” and “vertical” refer to the longitudinal central axis of the device. The terms “top”, “bottom”, “upper” and “lower” refer to the upright position of the device represented in FIGS. 3 and 4.

The principal subject matter of the present invention is a device which authorizes/prohibits the delivery of a dose by immobilizing/releasing the actuation of an actuator enabling a fluid product dispenser to be actuated.

The device for dispensing a fluid product shown in the figures comprises a fluid product dispenser 1, advantageously of a standard type. This dispenser 1 comprises a reservoir 2 containing the fluid product and a dispensing means 3, such as a pump or a valve, a portion of which is axially displaceable with respect to the reservoir 2. The dispensing means 3 is fastened to the reservoir 2 by means of a fixing ring 4. The dispensing means 3 is actuated when an actuator is displaced axially downwardly with respect to the reservoir 2. Generally, when the reservoir 2 does not contain propellant gas, a dispensing pump is used, and when the reservoir 2 contains propellant gas, a metering valve is used. These two types of dispensing means are well known to the person skilled in the art and since this dispensing means is not directly involved in the present invention, it will not be described in greater detail below.

The device for dispensing a fluid product also comprises an internal body 10, receiving the dispenser 1, and an external body 120, fixed to the internal body 10 and containing an electronic control module 90.

The internal body 10 comprises a hollow cylinder 11 which is axially open on the lower side, with coupling means which are advantageously in the form of a thread 12 on the outer surface of the lower opening. The hollow cylinder 11 is intended to receive the reservoir 2 of the dispenser 1. A cap 5 is provided in order to fix the dispenser 1 in the internal body 10. This cap 5 comprises complementary coupling means, advantageously produced in the form of an internal thread 6 which is adapted to cooperate with the coupling means of the internal body 10. Thus, in order to assemble the dispenser 1 in the device, the reservoir 2 is inserted inside the hollow cylinder 11 of the internal body 10. The cap 5 is then screwed onto said internal body 10. The method of assembly is shown in FIG. 2. This mode of operation means that it is easy to replace an empty reservoir in a dispenser 1 with a full dispenser. The device, and in particular the electronic control module 90, may then be reusable instead of being discarded.

On the upper side, the internal body 10 comprises a plate 13 and a hollow axial extension 14, extending axially upwardly from said plate 13. This hollow axial extension 14 has a reduced radial dimension compared with the internal diameter of said hollow cylinder 11. It may be moulded integrally with the internal body 10, or it may be manufactured separately and then secured to said internal body 10 in any appropriate manner. When the dispenser 1 is disposed in the internal body 10, at least a portion of the dispensing means 3 passes through said hollow axial extension 14.

The external body 120 is hollow and may have any external shape. In the example shown, the external body 120 is approximately rectangular in shape, which corresponds in part to the shape of said plate 13 of the internal body 10. The external body 120 is fixed to the internal body 10 in an appropriate manner, for example by snap fitting. Advantageously, the external body 120 comprises one or more windows 121, for example a window as shown in FIGS. 1 to 4, enabling a screen 91 of the electronic control module 90 to be viewed. This screen may display information, for example, instructions for use, battery charge information, etc.

The external body 120 also includes an opening 122 for receiving a control button 85. In a variation, the control button could be replaced by a control zone on the screen 91 or on another display visible in another window. This control zone could incorporate fingerprint detection means to authorize the actuation of the device only to the authorized person or persons, and thereby prevent any accidental actuation, for example by children. Other recognition means could be envisaged, such as facial recognition. The control button or control zone could also be replaced by other means: voice command, remote unlocking by a third party (for example a doctor) or command managed by a timer or software of the electronic control module.

A cover 30 is provided for fastening to the plate 13 of the internal body 10, said cover 30 comprising a hollow cylinder 31 and a radial flange 32. The hollow cylinder 31 comprises an internal profile 35, comprising a first window 350 and a second window 351, separated from the first window 350 by a radial strut 352. In a variation, the profile 35 could be provided on the internal body 10.

An actuator 20, provided with a dispensing orifice 21, is assembled in the hollow cylinder 31 of said cover 30, it being axially displaceable with respect to the internal body 10 between a rest position and an actuating position, in which the actuator 20 is displaced axially downwardly with respect to the internal body 10. Advantageously, the actuator comprises a nasal tip 22 which terminates at its upper end in the dispensing orifice 21 and which comprises, on the lower side, an axial skirt 23 provided with a radial bearing surface 230 which the user can press in order to actuate the dispenser 1. At least one axial tab 24 extends axially downwardly from the lower radial edge 231 of said axial skirt 23, in order to fix the actuator 20 in the hollow cylinder 31 of the cover 30, for example by snap fitting. In the example of FIG. 8, there are two radially flexible tabs 24, which are diametrically opposed. An axial finger 27 also extends axially downwardly from the lower radial edge 231 of said axial skirt 23, the function of which will be described below. In the example of FIG. 8, this axial finger 27 is disposed at 90° from each of the two diametrically opposed axial tabs 24.

Inside, the actuator 20 comprises a hollow tube 25 which will cooperate with the dispensing means 3 and which opens into the dispensing orifice 21, advantageously with a spray profile provided just upstream of said dispensing orifice in order to generate a spray. At least one axial strut 26 is provided below said radial bearing surface 23. In the example of FIG. 8, there are four axial struts 26 (three of which are visible), distributed around the periphery. The function of these axial struts will be described below.

The device further comprises a locking ring 40, a gear wheel 50 cooperating with said locking ring 40, a spring 60 for said locking ring 40, and a motor wheel 70 associated with a motor 80, said motor wheel 70 cooperating with said gear wheel 50.

The locking ring 40, the gear wheel 50, the spring 60 and the motor wheel 70 are disposed on the plate 13 of the internal body 10 and held in place by the cover 30.

The locking ring 40 is rotatably mounted about said axial extension 14 of the internal body 10 between a locking position and a release position. The spring 60 urges the locking ring towards its locking position. It is advantageously fixed on the one hand to a stud 46 of the locking ring 40 and on the other hand to a second stud 36 provided on the plate 13 of the internal body 10, as can be seen in FIGS. 13 and 15. The locking ring 40 cooperates with the actuator 20 for selectively immobilizing against or enabling the axial displacement of said actuator 20.

Figures 22, 23, 24, 25, 26:
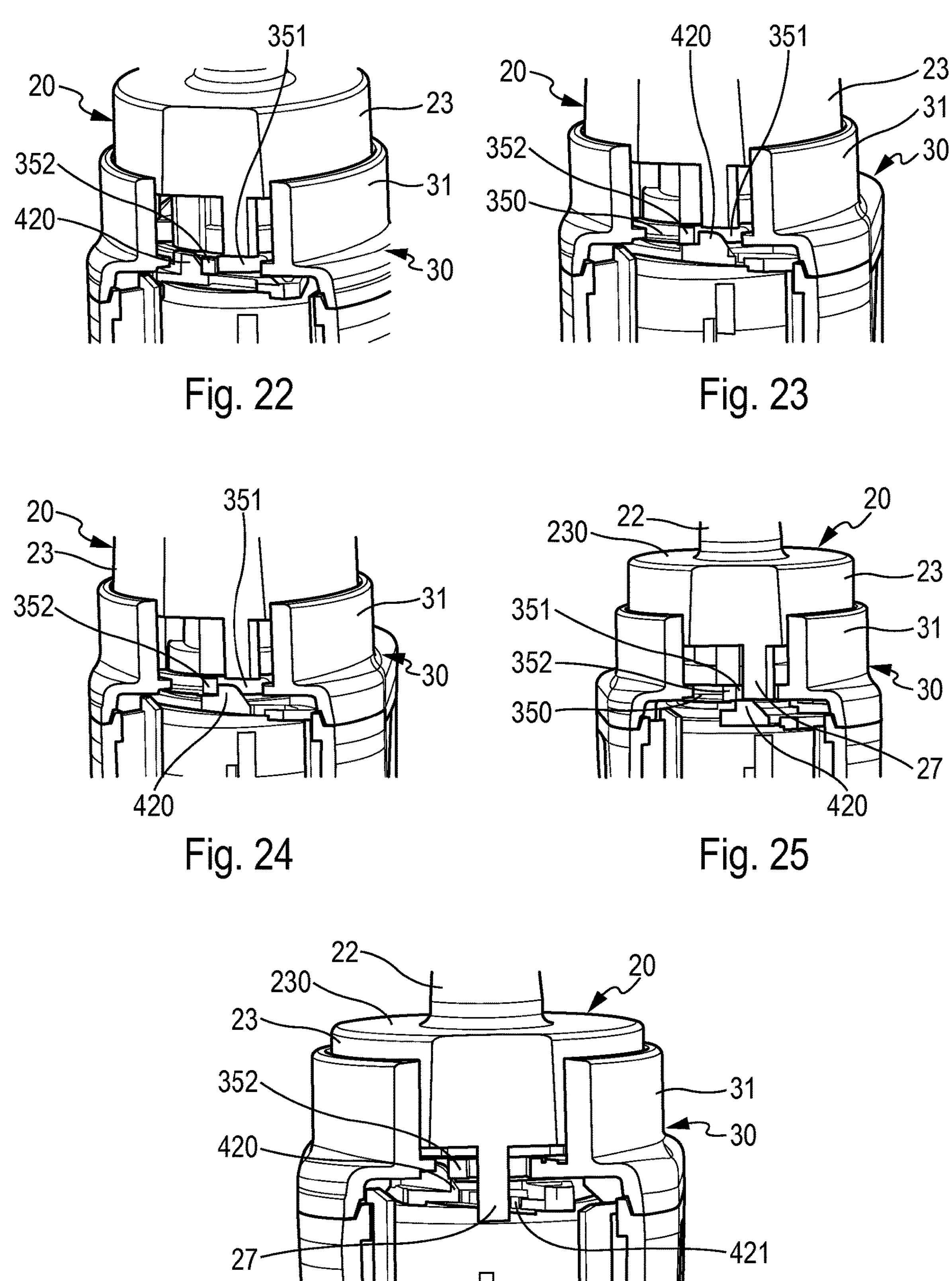

The locking ring 40 comprises a hollow sleeve 41 provided, at a lower axial edge 411, with an axially flexible tongue 42 extending coaxially and radially on the exterior of said hollow sleeve 41. This axially flexible tongue 42 comprises a tooth 420 which projects axially upwardly, and an opening 421 disposed behind said tooth 420. In the locking position of the locking ring, the tooth 420 is disposed in the first window 350 of the cover 30, as can be seen in FIGS. 17, 19, and 22. When the locking ring 40 is displaced towards its release position, the axially flexible tongue 42 deforms axially downwardly, as indicated by the arrow in FIG. 19, in order to enable the tooth 420 to pass under the radial strut 352 of the cover 30, so that it comes into position in the second window 351, as can be seen in FIG. 18. Advantageously, during the unlocking cycle, the rotation of the motor 80 transmitted by the gear wheel 50 creates an angular over-travel of the locking ring 40 and therefore an offset between the tooth 420 and the radial strut 352, as can be seen in FIG. 23. This can be used to ensure that the tooth 420 will snap behind the radial strut 352 when the motor 80 no longer exerts a torque, while the second set of teeth 52 of the gearwheel 50 is no longer engaged with the teeth 45 of the locking ring 40. This makes it possible to ensure reliable operation in spite of manufacturing tolerances for the various parts. Because the spring 60 urges the locking ring 40 towards its locking position, as soon as the locking ring 40 comes into its release position, the spring will attempt to return it to its locking position, but this displacement will be blocked by the radial strut 352 against which the tooth 420 of the flexible tongue 42 will abut, as can be seen in FIG. 24.

The locking ring 40 comprises at least one radial projection 43 extending radially outwards from said hollow sleeve 41. In the example in the figures, there are four radial projections 43 distributed around the periphery of the hollow sleeve 41. In the locking position, these radial projections 43 cooperate with the axial struts 26 of the actuator 20 in order to prevent the axial displacement of the actuator towards its actuating position. In contrast, in the release position, each radial projection 43 is angularly offset with respect to the respective axial strut 26, thus enabling an axial displacement of said actuator 20 towards its actuating position. The embodiment shown in the drawings, with four radial projections 43 cooperating with four axial struts 26, which can be seen in FIG. 15, makes the device particularly robust and prevents any unauthorized actuation of the device.

On the side opposite to the flexible tongue 42, the locking ring 40 comprises a flat 44 which supports teeth 45 which cooperate with the gear wheel 50 when the gear wheel moves the locking ring 40 towards its release position. The flat 44 also advantageously supports the stud 46 fixed to the spring 60. Advantageously, the locking ring 40 comprises detection means adapted to cooperate with the electronic control module 90 in order to inform it of its position. In the example shown, these detection means comprise an axial extension 47 extending axially downwardly from said flat 44.

The gear wheel 50 comprises a first set of teeth 51 comprising a plurality of teeth distributed over the entire periphery of the gear wheel 50. Axially above the first set of teeth 51, the gearwheel 50 comprises a second set of teeth 52. This comprises teeth only over a portion of the periphery. In the example shown in FIG. 10, the second set of teeth 52 comprises three teeth. This second set of teeth 52 cooperates with the teeth 45 of the locking ring 40, in order to cause it to rotate from its locking position towards its release position, as can be seen in FIGS. 20 and 21.

The motor wheel 70 comprises a set of teeth 71 cooperating with the first set of teeth 51 of the gear wheel 50. Thus, when the motor 80 causes the motor wheel 70 to rotate in one direction of rotation, this wheel causes the gear wheel 50 to rotate, driving the locking ring 40 from its locking position towards its release position.

An electronic control module 90 is fixed to a support body 81, which in turn is fixed to the internal body 10, the assembly being received inside said external body 120. This electronic control module 90 controls a motor 80, which is also fixed to the support body 81, and which cooperates with the motor wheel 70 in order to cause it to rotate.

The motor 80 may be a 3V DC gear motor adapted to cause a shaft of the motor connected to the motor wheel 70 to rotate. This motor may be powered in any appropriate manner, for example by means of rechargeable or non-rechargeable batteries or accumulators. Preferably, when the motor 80 is controlled, it causes the motor wheel 70 to turn in such a manner that the gear wheel 50 executes a complete revolution. This firstly causes the locking ring 40 to rotate from its locking position towards its release position, then disengages the second set of teeth 52 of the gear wheel 50 from the teeth 45 of the locking ring 40. Thus, once the locking ring 40 is in its release position, it is no longer connected to the motor 80.

The electronic control module 90 comprises appropriate electronic elements, in particular such as a microprocessor, in order to cause the device to operate, in particular the motor 80 and the screen 91. Advantageously, the electronic control module 90 comprises switches (not shown) for detecting the displacement and/or the position of the locking ring 40, in particular its axial extension 47. It is therefore possible to detect various actuation phases, in particular the return of the locking ring 40 to its locking position, after actuation of the dispenser 1 and therefore dispensing of a dose of fluid product. This information may be used to immobilize the device for a predetermined time.

Thus, the electronic control module 90 may comprise time delay means to allow a fresh actuation only after the expiry of a predetermined time delay. These time delay means may in particular comprise the internal clock of the microprocessor. Optionally, it is possible to add a real time clock component to it. This temporary immobilization preferably acts on the control of the motor 80, thereby preventing the motor from rotating in order to displace the locking ring 40 from its locking position towards its release position. In a variation, the control button 85 itself may be deactivated or immobilized for a predeterminable time. Advantageously, only authorized persons, such as medical personnel, can modify said immobilization time by having access to the electronic control module or via the screen 91. Advantageously, the screen 91 indicates how much time remains before it is possible and/or necessary to take the next dose. Optionally, an audible and/or visual signal may also be provided if the user nevertheless presses the control button in order to attempt to unlock the device.

The operation of the device shown in the drawings will now be described in more detail.

In a normal actuation cycle, the user takes the device in their hand in the rest position, shown in FIG. 3. In this position, the actuator 20 cannot be displaced axially downwardly because the actuator is immobilized by the locking ring 40 which is in the locking position.

To actuate the device, the user must first send a command to the electronic control module 90 to displace the locking ring 40 from its locking position towards its release position. To do this, they press the control button 85, in the example of the drawings, in the direction of the arrow F1 in FIG. 3. This pressure will cause the motor 80 and therefore the motor wheel 70 to rotate, which will cause the gear wheel 50 and therefore the locking ring 40 to rotate from its locking position, visible in FIGS. 15, 17, 19 and 22, towards its release position, visible in FIGS. 16, 18 and 23. This displacement of the locking wheel 60 will load the spring 60, which will then act to return the locking ring 40 towards its locking position. However, since the locking ring 40 is immobilized in the release position by the tooth 420 which abuts against the radial strut 352 of the cover 30, it cannot return to its locking position under the effect of the force exerted by the spring 60.

The user can then exert an axial actuating force on the actuator 20 in order to displace it axially downwardly in the direction of the arrow F2 in FIG. 4. This will actuate the dispensing means 3 and expel a dose of fluid product through the dispensing orifice 21. The actuation of the motor 80 has caused the gear wheel 50 to rotate through a complete revolution, in a manner such that in the release position, the locking ring 40 is no longer connected to the motor 80, since the second set of teeth 52 of the gear wheel 50 is no longer connected to the teeth 45 of the locking ring 40. In a variation, the gear wheel 50 does not make a complete revolution each time the motor 80 is actuated, but rather any angular path, for example a half turn. In this case, the number of teeth 45 of the locking ring 40 and the number of teeth of the second set of teeth 52 of the gear wheel would be adapted accordingly.

From the start of actuation, the actuator 20 descends axially with respect to the locking ring 40, with the axial finger 27 of the actuator which will cooperate with the tooth 420 of the flexible tongue 42. As can be seen in FIG. 25, the axial finger 27 will push the tooth 420 axially downwardly, so that the tooth will disengage from the radial strut 352. When the tooth 420 is no longer immobilized by the radial strut 352, the locking ring 40 is urged towards its locking position by the spring 60. However, it cannot return to this locking position since the radial projections 43 of the locking ring 40 remain immobilized against the radial struts 26 of the actuator 20, in an intermediate position visible in FIG. 28. It is only when the actuator 20 has returned to its rest position that the locking ring 40 can automatically return to its locking position under the effect of the spring 60. Preferably, the disengagement of the tooth 420 from the radial strut 352 occurs at the start of the actuation stroke of the actuator 20, which ensures locking even in the event of an incomplete actuation stroke. It is therefore not possible to dispense several consecutive partial doses. After disengaging the tooth 420, when the locking ring 40 is in the intermediate position of FIG. 28, the actuator 20 can continue its complete actuation stroke to its actuating position, with the axial finger 27 passing through the opening 421 of the flexible tongue 42, as can be seen in FIG. 26.

After actuation, the user releases the pressure on the actuator 20, which will be returned towards its rest position by the dispensing means 3; in particular its return spring (not shown).

The device is then returned to its rest position, and a subsequent actuation will only be possible after the expiry of the immobilization time which has been predetermined by the electronic control module 90.

Although the present invention has been described above with reference to an advantageous embodiment, it is clear that various modifications may be made thereto by the person skilled in the art without departing from the scope of the present invention as defined in the accompanying claims.

The invention claimed is:

1. A device for dispensing a fluid product, comprising:

a fluid product dispenser comprising a reservoir containing fluid product and a dispensing means mounted on said reservoir, an internal body comprising a hollow cylinder receiving said dispenser, an actuator provided with a dispensing orifice, mounted in order to be axially displaceable on said internal body between a rest position and an actuating position, the axial displacement of said actuator from its rest position to its actuating position actuating said dispensing means in order to dispense a dose of fluid product through said dispensing orifice, wherein said device comprises:

a motor, an electronic control module, a gear wheel connected to said motor and driven in rotation by said motor, and a locking ring which is rotatably mounted on said internal body between a locking position and a release position, a spring urging said locking ring towards its locking position, said locking ring being displaced from its locking position towards its release position by said gear wheel, said locking ring cooperating in the locking position with said actuator in order to prevent its axial displacement and cooperating in the release position with said actuator in order to enable its axial displacement towards its actuating position;

wherein said locking ring comprises an axially flexible tongue provided with an axially upwardly projecting tooth; and wherein said internal body, or an element integral with said internal body, comprises an internal profile comprising a first window and a second window which is separated from said first window by a radial strut.

2. The device as claimed in claim 1, comprising an external body fixed to said internal body and containing said motor and said electronic control module.

3. The device as claimed in claim 1, comprising a control button for initiating the actuation of said motor.

4. The device as claimed in claim 1, in which said actuator comprises at least one axial strut and said locking ring comprises at least one radial projection.

5. The device as claimed in claim 4 in which, in the locking position of said locking ring, said at least one radial projection cooperates with said at least one axial strut in order to prevent the axial displacement of said actuator towards its actuating position, and in the release position of said locking ring, said at least one radial projection is angularly offset from said at least one axial strut, thereby enabling said actuator to be displaced axially towards its actuating position.

6. The device as claimed in claim 5, comprising four radial projections and four axial struts, each radial projection cooperating with a respective axial strut in order to immobilize the axial displacement of said actuator in the locking position of said locking ring.

7. The device as claimed in claim 1, in which said actuator comprises an axially downwardly extending axial finger.

8. The device as claimed in claim 7 in which, in the locking position of said locking ring, said tooth is disposed in said first window, the displacement of said locking ring towards its release position axially deforming said flexible tongue in order to enable said tooth to pass into the second window behind said radial strut, said radial strut then cooperating with said tooth in order to prevent said locking ring from returning to the locking position under the effect of said spring.

9. The device as claimed in claim 8 in which, during the axial displacement of said actuator from its rest position towards its actuating position, said axial finger cooperates with said tooth by pushing it axially downwardly in order to disengage it from said radial strut, thereby enabling said locking ring to return towards its locking position.

10. The device as claimed in claim 9 in which, while said actuator is displaced from its rest position, said actuator immobilizes said locking ring in an intermediate position between its release position and its locking position.

11. The device as claimed in claim 1 in which, at the end of actuation, when said actuator returns to its rest position, said locking ring automatically returns to its locking position under the effect of said spring.

12. The device as claimed in claim 1, in which said electronic control module comprises time delay means in order to prevent the displacement of said locking ring from its locking position towards its release position for a predeterminable time after each actuation of the dispenser.

13. The device as claimed in claim 12, in which said time delay means immobilizes a control button of the device and/or said motor.

14. The device as claimed in claim 1, wherein the dispensing means is a pump or a valve.

15. The device as claimed in claim 1, wherein said internal body, or an element integral with said internal body, is a cover.

* * * * *